United States Patent [19]

Mizuuchi et al.

[11] Patent Number: 4,716,105
[45] Date of Patent: Dec. 29, 1987

[54] MINI MU CONTAINING PLASMID AND A METHOD FOR RAPID DNA SEQUENCING

[75] Inventors: Kiyoshi Mizuuchi; Michiyo Mizuuchi; Toshiro Adachi, all of Bethesda, Md.

[73] Assignee: The United States of America as represented by the Department of Health and Human Services, Washington, D.C.

[21] Appl. No.: 680,992

[22] Filed: Dec. 13, 1984

[51] Int. Cl.[4] ......................... C12Q 1/70; C12Q 1/68; C12N 15/00

[52] U.S. Cl. .......................................... 435/5; 435/6; 435/172.3; 435/320

[58] Field of Search ...................... 435/317, 172.3, 91, 435/6, 5; 935/9, 10, 77

[56] References Cited

PUBLICATIONS

Ray et al., Gene, 4:109–119, 1978.
Gijsegem et al., Plasmid 7:30–44, 1982.
Mizuuchi, et al., "The Extent of DNA Sequence Required for a Functional Bacterial Attachment Site of Phage Lambda", Nucleic Acids Research, 13:1193–1208 (1985).
Craigie, et al., Cloning of the A Gene of Bacteriophage Mu and Purification of Its Product, the Mu Transposase, J. of Biol. Chem. 260:1832–35 (1985).
Mizuuchi, In Vitro Transposition of Bacteriophage Mu: A Biochemical Approach to a Novel Replication Reaction, Cell. 35:785–94 (12/83).
Maxam et al., A New Method for Sequencing DNA. Proc. Natl. Acad. Sci., 74:560–64 (1977).
Sanger et al., Cloning in Single-Stranded Bacteriophage as an Aid to Rapid DNA Sequencing. J. Mol. Biol., 143:161–178 (1980).
Biggin, et al., Buffer Gradient Gels and [35]S Label as an Aid to Rapid DNA Sequence Determination. Proc. Natl. Acad. Sci., 80:3963–65 (1983).
Sanger, et al., DNA Sequencing with Chain-Terminating Inhibitors., 74:5463–67, (1977).

Primary Examiner—Thomas G. Wiseman
Assistant Examiner—Thomas D. Mays
Attorney, Agent, or Firm—Holman & Stern

[57] ABSTRACT

The present invention discloses a rapid method of sequencing a relatively large segment of deoxyribonucleic acid. The method in part comprises high frequency insertion of a suitable transposon into a segment of DNA of interest. Preferable use of Mu transposons is described. A plasmid having mini-Mu transposons has been prepared and disclosed.

12 Claims, 4 Drawing Figures

FIG. 4

MINI MU CONTAINING PLASMID AND A METHOD FOR RAPID DNA SEQUENCING

BACKGROUND OF THE INVENTION

1. Technical Field

The present invention is related to a plasmid having mini Mu transposons and a method of rapid DNA (deoxyribonucleic acid) sequencing. More particularly, the present invention is directed to the use of random insertion of transposons as a part of rapid and convenient process related to DNA sequencing.

2. Prior Art

Since the development of DNA sequencing techniques, several refinements and improvements have occurred in sequencing methodology and there are a number of approaches available for different sequencing requirements.

The most critical step in sequencing method is the set of four nucleotide specific sequencing reactions. Each one of the reactions produces a group of radioactively-labelled DNA fragments, one end of which is fixed (starting point) and the other ends are distributed among the locations of one of the four nucleotides along the DNA. The products of the set of four reactions are then separated side by side by a gel electrophoretic method, which separates each DNA fragment according to its length, and visualized by autoradiography. The autoradiogram reveals the positions of each of the four nucleotides as the distance from the fixed (starting) point, thus the nucleotide sequence adjacent to the fixed point can be determined.

Two different methods are now available for the sequencing reaction: one is the nucleotide specific chemical modification and cleavage reactions of Maxam and Gilbert, PNAS, 74:560, 1977, and the other is the primer extension reactions in the presence of nucleotide specific chain terminators as described by Sanger et al., PNAS 74:5463, 1977. Although it has been used widely and is still an important method, the chemical method of Maxam and Gilbert, supra, is more suited for sequencing of relatively short and wel-defined DNA pieces because of its relatively labor-intense nature.

At present, the chain terminator method of Sanger et al., supra, has gained wide acceptance as the method of choice for determining the base sequence of a long stretch of unknown DNA.

Since the length of DNA sequence, that can be determined conveniently by one round of either of the two sequencing methods available at the present time, is limited to about 300 base pairs, one has to set up many rounds of sequencing reactions to determine the sequence of a large piece of DNA. Each round uses a different starting point along the DNA, preferably several hundred bases away from its neighbors. For the base specific chain terminator method of Sanger et al., supra, the starting point is the end of the primer sequence used, or rather the end of the unknown sequence that is joined artificially to a universal primer sequence on a proper cloning vector.

Thus, for the determination of a long stretch of unknown sequence, the first step necessary is to generate a library of clones of the DNA to be sequenced. Each member of the library must have a unique starting point for sequencing that is within the range of sequence determination from the neighboring starting point in another member of the library, so that the sequence segments overlap and can be assembled into one continuous piece.

An often used method presently known for determining the sequence of a long stretch of unknown DNA may be outlined as follows.

The DNA segment of interest is randomly fragmented into small pieces which are cloned into phage M13 cloning vectors; the viral DNA of each clone is then used as a template in combination with a synthetic universal sequencing primer oligonucleotide in the chain terminator sequencing reaction; the reaction products made in the presence of $^{35}$S-labelled substrate are separated by gradient gel electrophoresis, visualized by autoradiography and the sequence is analyzed and assembled with the help of computer means.

While the scheme just outlined is widely used, it has certain shortcomings. One of the major problems derives from the fact that the DNA segment to be sequence is first fragmented into small pieces (a few hundred base pairs). The preparation of random clones of the small pieces, although not an overwhelming task, is still an elaborate, complex and time-consuming step. Furthermore, there is no certainty that the set of clones used for sequencing would cover the entire length of the DNA. For instance, if at the step of sequence assembly a missing stretch is discovered, it is a tedious and complicated task to search the entire clone library for the missing clone(s) to fill in the missing link. This is because the information on the position of each subfragment within the original long DNA piece has been lost by the random subcloning process.

The present invention discloses a rapid and convenient method which inter alia solves the problems mentioned above by using random insertion of transposons, particularly a mini Mu transpon, into a large cloned piece of DNA, instead of the random cloning of small fragments.

Random insertions of the transposon can be done by very simple steps using in vivo reactions in *Escherichia coli* cultured cells. This brings a substantial time saving. Since the entire DNA segment of interest remains intact without fragmentation in small pieces as is required in the hitherto known conventional process it is easy to assess which part of the segment has been sequenced during the process by analyzing the mini Mu insertion site. This is a great advantage when the sequence of a large segment of DNA has to be determined.

SUMMARY OF THE INVENTION

It is, therefore, an object of the present invention to provide a method for rapid sequencing of DNA segments of various sizes without fragmentation thereof.

It is another object of the present invention to provide a convenient and efficient method of sequencing large segments of DNA, particularly DNA segments ranging from about 300 base pairs to about 5 kilo base pairs or longer.

It is yet another object of the present invention to provide a plasmid having mini Mu transposon inserted in the DNA thereof.

Other objects and advantages of the present invention will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 4 shows a computerized assembly of base sequences determined from autoradiographs as shown in FIG. 3.

DETAILED DESCRIPTION OF THE INVENTION

These and other objects and advantages of the present invention are achieved by providing a plasmid having mini Mu transposons and a rapid method for sequencing of a DNA segment using said mini-Mu plasmid.

The term "mini-Mu" as used herein is defined as a segment of DNA that retains the capability to function as a Mu transposon and has shorter DNA segment than phage Mu. For the purpose of this invention the mini-Mu preferably has a length of DNA less than 2 kilobases.

The term "bases", "sequencing" and "DNA sequencing" as used herein means the determination of the sequence of purine and pyrimidine bases constituting deoxyribonucleic acid (DNA) segment of interest. The purines which are commonly found in DNA are adenine (A) and guanine (G) whereas the pyrimidines which are commonly found in DNA are cytosine (C) and thymine (T); so that a sequence analysis of DNA will comprise a repetitive occurrence and variation of these four bases symbolically designated as AGTC and the like.

The terms transposon, synthetic oligonucleotide, primer, vector, plasmid, genome, marker, phage, Mu and the like as used herein are defined to convey their well established ordinary meaning in the art to which they pertain and as may be found in many modern text book or publication related to molecular or biochemical genetics and genetic engineering, the same being incorporated herein by reference. Preferable among such publications are Toussaint et al, in Mobile Genetic Elements, ed. Shapiro, Academic Press, New York, pp. 105–158, (1983); Methods in Enzymology, vols. 68 (1979), 100 (1983) and 101 (1983), Academic Press, New York; and Bukhari et al. "DNA Insertion Elements, Plasmids, and Episomes", Cold Spring Harbor Laboratory, New York, (1977) all of which are incorporated herein by reference.

Figure 1:
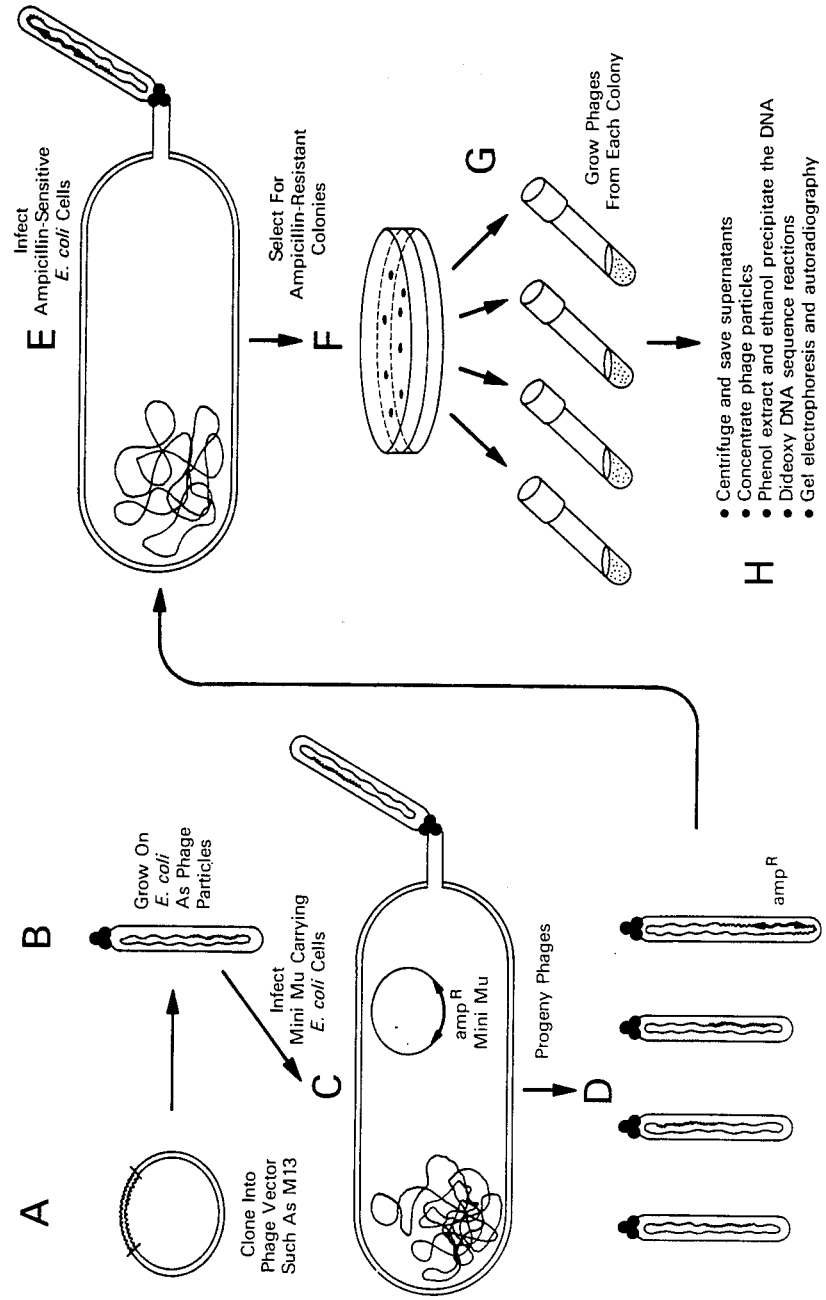
FIG. 1 is a schematic representation of various steps in the method disclosed in accordance with the present invention.

FIG. 1, summarizes the various steps, A through H, comprising the present invention.

A. The DNA segment of interest is cloned into a phage cloning vector. For this purpose an M13 phage-cloning vector is preferred. This vector can accommodate at least up to 5,000 base pairs of DNA to be sequenced at a time. However, the vector used for this invention is not limited to simple M13 system and other vectors specifically suited to make full use of this invention can also be advantageously employed. Examples of such vectors are any vector that can be grown as a single stranded DNA phage particles.

B. A phage stock of the above clone is then prepared.

C. An *Escherichia coli* (*E. coli*) strain that contains a mini Mu or any other suitable transposon which preferably carries a drug-resistance marker, and as small in overall size as possible (less than 2 kilobases), is then infected by (B), together with phage Mu to provide the necessary functions for mini Mu transposition. The type of transposon usable for this invention is, of course, not limited to mini Mu. However, the preferred use of the mini Mu transposon has an advantage over most other transposons, because of its high frequency of transposition. However, other transposons with a high enough transposition frequency can also be employed. The detailed structure of the mini Mu transposon is not critical. In the practice of the present invention, a mini Mu that carries only an ampicillin-resistance marker within the transposon (pAT38) is used, although a larger mini Mu that carries the same marker along with the ColEl (plasmid colicinogenic factor El) DNA replication origin (pMK108), can also be used for certain applications. The vector part that carries the transposon is also quite flexible, i.e., the invention is not restricted to the vector exemplified herein. As noted above, other suitable vectors can, of course, be employed. The means of providing the necessary functions for mini Mu transposition is also not limited to the infection by phage Mu. The genes for this function can be cloned into regulatable expression vector and placed within the host *E. coli* strain permanently along with the mini Mu.

D. After about an hour, a phage stock is obtained that contains transducing phage particles for the drug-resistance marker used. These transducing phage DNA's carry the transposon DNA (mini Mu DNA) inserted randomly into the DNA described in (A).

E. Appropriate *E. coli* cells are infected with the phage stock of (D) and plated on selection plates for the appropriate resistance marker.

F. This step selects the clones that carry the drug-resistance transducing phage DNA described in (D).

G. Small scale cultures are prepared from individual colonies. When the M13 cloning vector is used in step (A), several hours of aeration produces an appropriate phage stock. The cultures are centrifuged and the supernatants that contain the transducing phage are saved. When the cloning vector used in step (A) is designed to yield clones carrying defective transducing phage DNA at this stage, a helper phage is superinfected at this stage to obtain the phage stock.

H. From this stage on, this method uses the base-specific chain terminator method of Sanger et al, supra, for DNA sequence determination reactions, and the standard gel electrophoresis method for the resolution of the reaction products in order to read the sequence is used.

In general, phage particles are precipitated by polyethyleneglycol (PEG), phenol extracted, and ethanol precipitated to yield substantially purified DNA which is used as the template for the sequencing reaction. The term substantially purified means that it is as purified as suitable for its use in the following sequencing reactions. This DNA is then hybridized with an oligonucleotide DNA primer of the transposon end sequence. The complex is mixed with reaction cocktails that contain four deoxynucleoside triphosphates, one of four dideoxynucleoside triphosphates (the chain terminator) and a radiolabelled deoxynucleoside triphosphate. DNA polymerase I (Klenow fragment) is used to elongate the primer; the product can be terminated at each specific base position. The reaction products are separated by routine denaturing acrylamide gel electrophoresis and the sequence of the DNA segment is read from an autoradiograph, and assembled optionally with the aid of computer analysis.

It should be noted that an essential feature of the invention described herein is the use of a transposon, such as mini Mu, for the generation of a clone library. Any suitable transposon may be used in the practice of the present invention, mini-Mu being only a preferred embodiment. Up to a point where multiple transposition into a single phage DNA becomes a problem, the higher the frequency of transposition the more preferred the transposon would be.

Figure 2:
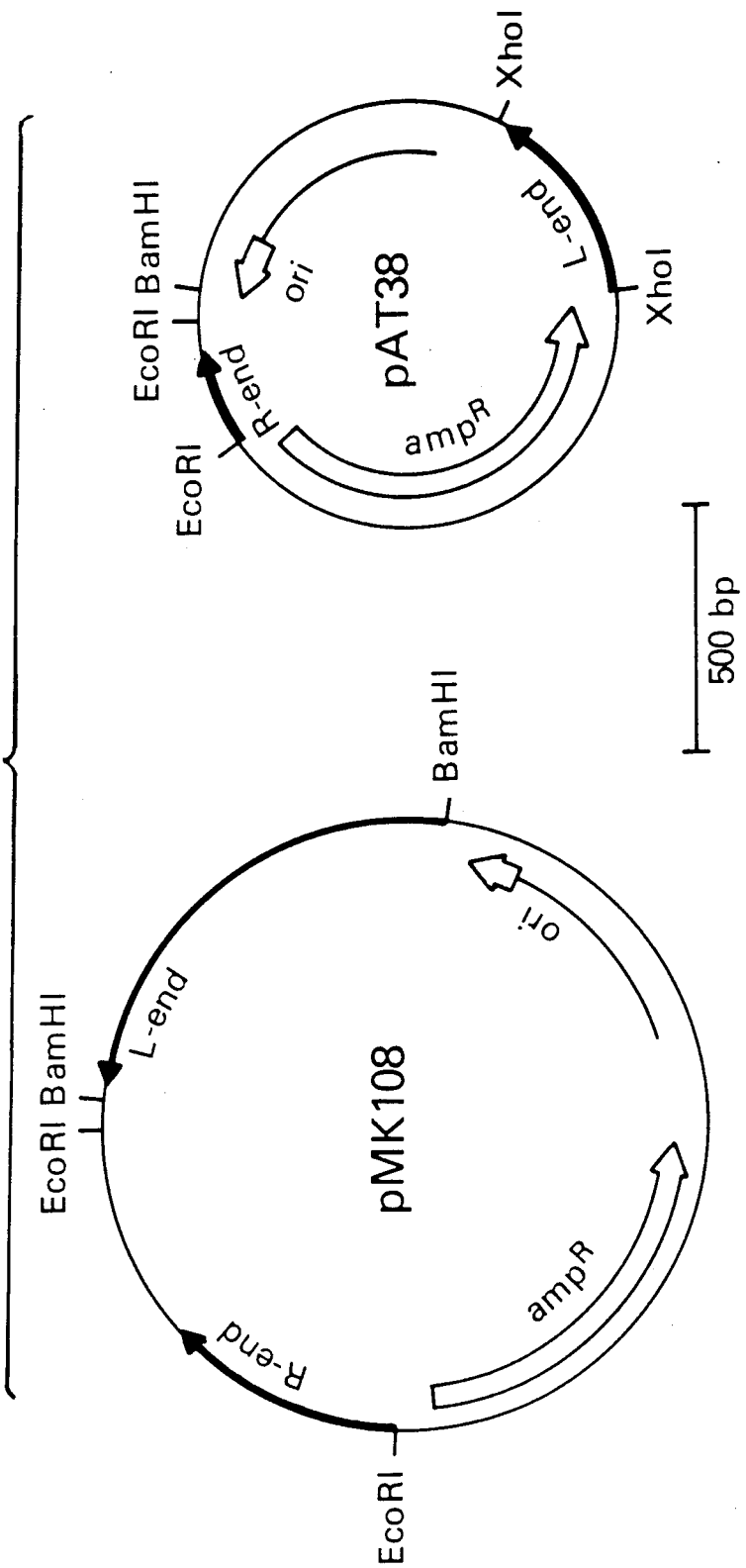
FIG. 2 illustrates representative mini-Mu constructions showing various segments in two different plasmids.

Mu is a temperate bacteriophage which uses a tansposition reaction at several stages in its life cycle. The frequency of transposition exibited by Mu is highest among known transposons. Mu can insert itself almost randomly into other DNA sequences. The two Mu-end sequences are needed to form a mobile DNA structure which can transpose in the presence of two phage specified gene products, the Mu A and B proteins along with other $E.$ $coli$ proteins. One can construct mini Mi transposons carrying drug-resistance markers by flanking the resistance gene with the two Mu-end sequences as shown in FIG. 2. Construction of such mini Mu transposons is well known in the art and the methods involved in such construction process have been described by Maniatis et al, in "Molecular Cloning: A Laboratory Manual; (1982)", Cold Spring Harbor, N.Y., which is incorporated herein by reference. A mini Mu transposon in a plasmid will transpose if the necessary protein functions are supplied either by inducing the genes for the functions located within the same plasmid or located somewhere else in the cell or by infecting with phage Mu. Thus, if one infects an $E.$ $coli$ strain carrying a mini Mu transposon with a phage carrying a cloned piece of DNA to be sequenced, together with phage Mu as the donor of the necessary phage coded functions, then among the resulting progeny will be transducing phages in which the drug-resistant mini Mu transposon has inserted itself into the cloned piece of DNA of interest within the infecting phage genome. By using the phage lysate to transduce a second $E.$ $coli$ strain sensitive to the marker drug, one can isolate the marker-drug resistant, mini-Mu transposed phage particles carrying the cloned DNA of which the base-sequence needs to be determined. If one uses a single-stranded DNA phage such as M13 as the vector, the viral DNA of each transducing phage can directly be used, in combination with a synthesized oligonucleotide primer complimentary to the Mu-end sequence, for the chain terminator sequencing method of Sanger et al, supra. to identify the base sequence.

All publications or references cited hereunder are incorporated herein by reference. Preferred materials and methods are now described.

MATERIALS AND METHODS

Bacterial strains, phages, and plasmids $E.$ $coli$ strains used in this disclosure are all derivatives of JM103 or JM105 as described by Messing, in Methods in Enzymology, Vol 101, Academic Press, New York, pp. 20-78, 1983. AT32 is JM103 mu$^R$; AT33 is AT32 (λcI857::Tn9) and AT40 is JM103 (pAT38). A parallel set of strains with JM105 background was also constructed and used for certain embodiments. Mu cts62 was used as the donor of Mu transposition functions. M13 mp8.gyrB and M13 mp19.gyrB carried 3.5 kilo base pairs of XMaI-HpaI fragment that contains the coding region of gyrB gene, cloned into M13 mp8 and M13 mp19 phage vectors (Messing, supra), respectively.

The mini Mu plasmid pAT38 shown in FIG. 2 was constructed from three pieces. The vector part was modified from pMM306 by replacing a 19 base pair AhaIII fragment (position 3232-3251 of the pBR322 sequence) with an XhoI linker (New England Biolabs). Mu-end fragments were obtained by cutting the DNA of another mini MU plasmid pMK108 (Mizuuchi, Cell 35:785-794, 1983) with RsaI in the presence of purified Mu A protein, which protects an RsaI site at position 19 of the Mu L-end. The 397 base pair RsaI fragment containing the L-end was purified and ligated to an XhoI linker. An RsaI fragment of about 290 base pairs contining the R-end was purified from the same digest and ligated to an EcoRI linker (Collaborative Reaearch). These Mu-end fragements were digested with XhoI or EcoRI and inserted at the appropriate restriction site on the vector DNA, following standard procedures as described by Maniatis et al, supra. A plasmid having mini Mu transposons and contructed in accordance with the present invention has been deposited in American Type Culture Collection, Rockville, MD and has been designated ATCC 39943.

Enzymes and Oligonucleotides.

DNA polymerase I (Klenow fragment) was obtained from IBI or Boehringer-Mannheim. Restriction endonucleases were obtained from New England Biolabs. T$_4$ DNA ligase was obtained from Boeringer-Mannheim. T$_4$ polynucleotide kinase was obtained from P-L Biochemicals. Mu A protein was purified as described by Craigie and Mizuuchi, Journal of Biological Chemistry, Volume 260, February 1985. Deoxynucleoside triphosphates and dideoxynucleoside triphosphates were obtained from New England Biolabs. α-$^{35}$S-labelled deoxyadenosine α-thiotriphosphate (~1000 Ci/mmol) and $\sqrt{}$-$^{32}$P labelled adenosine triphosphate (~3000 Ci/mmol) were obtained from New England Nuclear.

Several oligonucleotide primer sequences were synthesized by phosphoramidite chemistry using a Biosystems 380 A automatic oligonucleotide synthesizer and purified by using a reverse phase column (Waters μ bond pack C18 or Hamilton PRP-1) and ethanol precipitation. The following sequences were used as the primer:

| | |
|---|---|
| L-end primer: | TTTTCGTACTTCAAG (position 27 to 13). |
| R-end primer: | TTTTCGCATTTATCGTG (position 49 to 33). |
| R-end primer: | TTTTTCGTGCGCCGCTT (position 19 to 3). |
| R-end primer: | GCATTTATCGTGAAACC (position 44 to 28). |

Transposition of mini Mu into M13 clone DNA.

The mini Mu carrying strain AT40 was grown to a cell density of 2×10$^8$/ml in L broth containing 2.5 mM MgSO$_4$ and 1 mM CaCl$_2$, at 37° C. A half ml of the culture was mixed wih Mu cts 62 phage to give multiplicity of infection (moi) of 4 and incubated at 42° C. for 15 min. M13 mp8.gyrB or m13 mp19.gyrB was added to a moi of 4 and the culture was aerated at 37° C. for 2 hours or until cell lysis occurred. A few drops of chloroform were added, the lysate was centrifuged at about 10,000×g for 5 min, and the supernatant containing the phage was saved.

Two microliters of the phage lysate were mixed with 1 ml of a log-phase culture ($2 \times 10^8$/ml) of AT32 (or AT33) in L broth and left standing at room temperature ($\approx 23°$ C.) for 30 min. One-tenth ml aliquots of the infected culture were plated onto L-agar plates containing 30 µg/ml of ampicillin for AT32 or 30 µg/ml each of ampicillin and chloramphenicol for AT33, and the plates were incubated at about 31° C. overnight.

One-and-a-half ml aliquots of 1:100 dilution of an overnight culture of AT32 in L-broth were distributed into test tubes. Each tube was also inoculated with a single colony of the amp$^R$ (or amp$^R$ cm$^R$ for AT33) cells. The test tubes were aerated vigorously for 5 hours at 37° C. Cultures were centriged at $10,000 \times g$ for 5 minutes and the supernatants containing M13 phages with the cloned fragment and mini Mu inserts were retained.

Preparation of the Viral DNA of M13 clone with mini Mu insert

M13 phages with the cloned fragment and a mini Mu insert were precipitated with polyethyleneglycol (PEG), extracted with phenol and the DNA was precipitated with ethanol as described by Sanger et al, J. Mol. Biol. 143 :161–178, 1980.

Sequencing Reaction

The primer extension mehtod of Sanger et al, supra involving a set of base specific chain terminators was used essentially as described. Primers used for this study were chemically synthesized oligonucleotides corresponding to the Mu end sequences. Both a L-end (Mu left end) primer and a R-end (Mu right end) primer were added together (3–4 ng each per set of four 6 µl reactions). For template DNA samples, for which the orientation of the mini Mu insert was determined prior to the sequencing reaction as described infra, one primer complementary to the proper end was added. $^{35}$S-labelled deoxyadenosine$\alpha$-thiotriphosphate (5 µci per reaction) was used as the radioactive precursor or substrate.

Gel electrophoresis

The reaction products were separated by a denaturing acrylamide gel electrophoresis as described by Biggin et al, PNAS, 80: 3963, 1983. A half mm thick buffer gradient 6% acrylamide gel (13 in $\times$ 16 in) was prepared and the gel was run on a buffer cooled sequencing gel elctrophoresis apparatus (Bio Rad) at 100 to 130 W (1500 to 2000 V), the voltage being adjusted to keep the upper buffer temperature at about 50°–55° C. After electrophoresis, the gel was transferred onto a piece of filter paper, rinsed with an aqueous solution of 5% acetic acid and 5% methanol and dried. An antoradiograph was prepared by exposing X-ray film to the gel without intensifying screen.

Screening of M13 clones for the orientation of mini Mu insert.

Three µl of the polyethyleneglycol (PEG) concentrated (ten-fold) stock phage suspension of the M13 clone with a mini Mu insert were mixed with 2–4 ng of $^{32}$P-end-labelled R-end or L-end oligonucleotide primer in 10 µl of 5% Ficoll, 5% SDS, 50 mM NaCl, 10 mM Tris.HCl pH 7.5, 10 mM EDTA and 0.02% BPB. The mixture was incubated at 100° C. for 4 min, at room ($\approx 23°$ C.) temperature for 45 min, and then chilled in ice and electrophoresed in a 1% agarose gel (3 mm $\times$ 10 cm) in tris-borate-EDTA buffer as described by Maniatis et al., supra at 80 V for 2 hours. The gel apparatus was kept in ice cold water during the electrophoresis. The gel was dried and an autoradigram was prepared with a typical exposure time of an hour. The M13 clones that carry mini Mu inserts exhibit a radioactive band indicative of hybridization of the single-stranded viral DNA with one of the two radioactively labelled Mu-end primers.

Since the two Mu-end oligonucleotide primers carry the sequences of opposite strands of Mu DNA, only one of the two primers can hybridize with a given 13 clone with a mini Mu insert. This test unambiguously determines the orientation of each mini Mu insert and the primer to be used for sequencing reaction.

Figure 3:
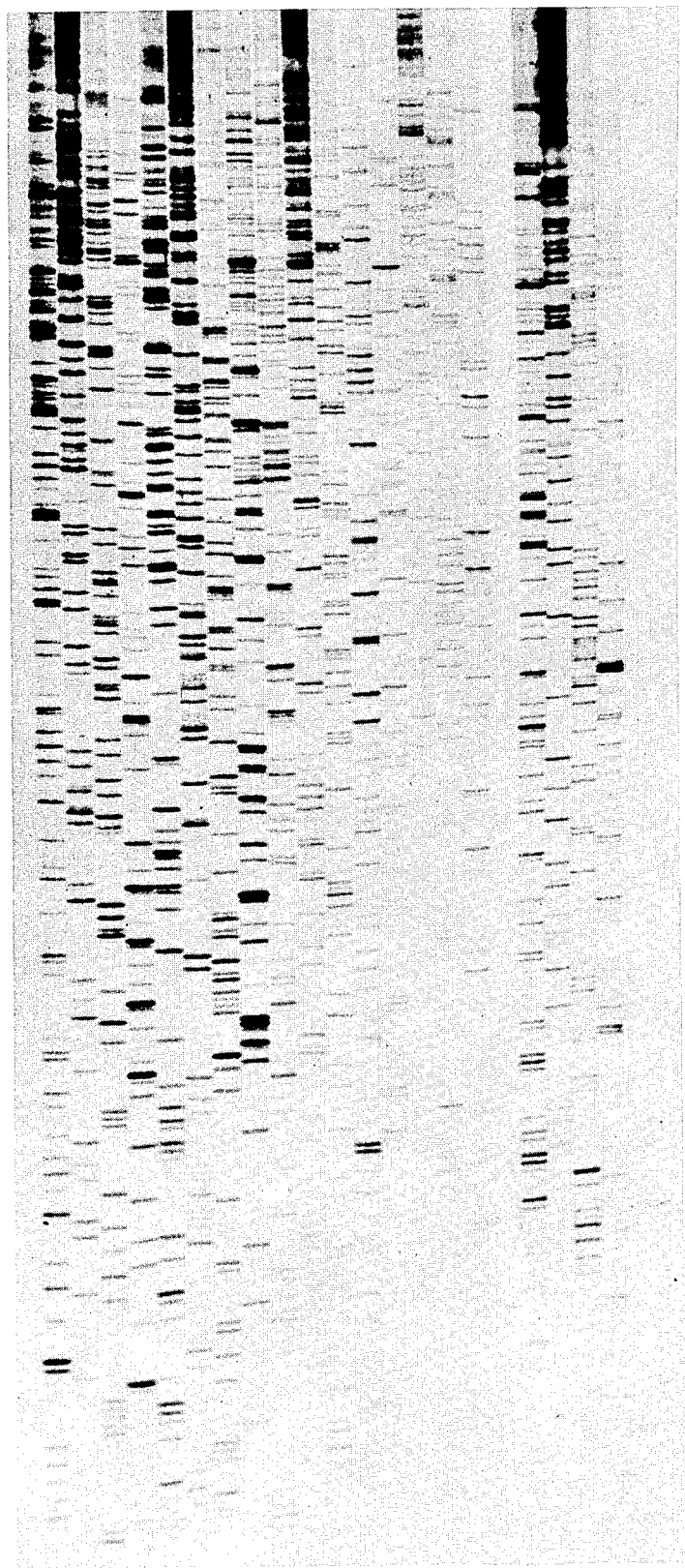
FIG. 3 represents a typical autoradiograph of gel electrophoresis of a DNA segment analyzed in accordance with the present invention.
Figure 4:
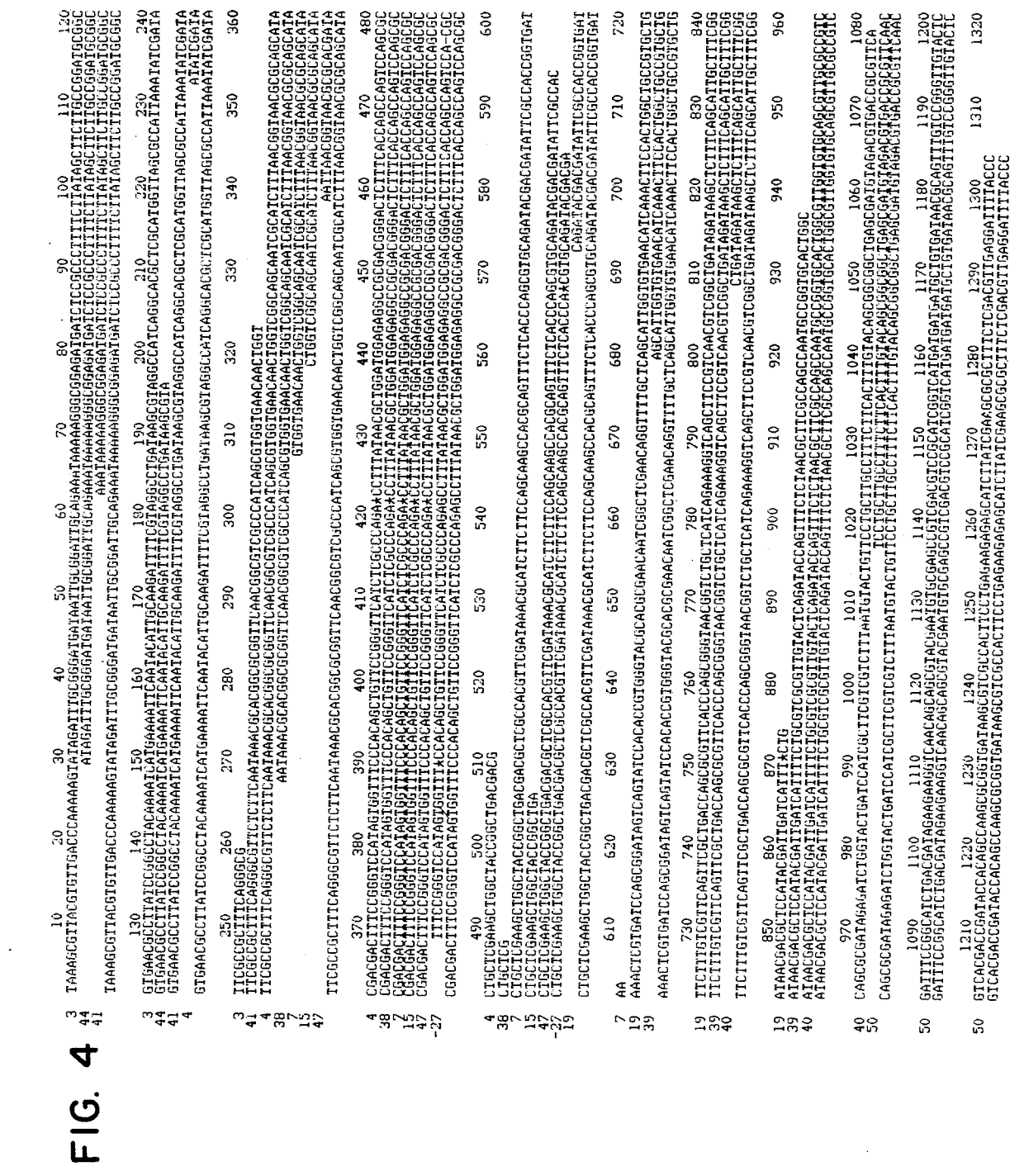

FIG. 3 shows an example of the sequencing gel pattern obtained by the method described herein. As shown, from 30 usable gel readings with aggregate length of 6939 bases, 2951 base long sequence has already been determined. A part of the sequence is shown in FIG. 4.

Heretofore, all methods of generating the library of subclones needed for the base specific chain terminator sequencing method of Sanger et al supra, required in vitro insertion of subfragments into a cloning vector DNA. In contrast, according to the method of the present invention, the library is generated without fragmentation by random insertion of a transposon (mini Mu) DNA into the intact segment of DNA of interest, cloned into an M13 vector. Since this process utilizes the entire intact DNA segment through efficient in vivo transposition reaction, it can be carried out by a simple cycle of quick phage infection steps. Each member of the library carries the entire cloned DNA segment of interest, into which a copy of the mini Mu DNA is inserted. The point of insertion is essentially random. The viral DNA of each mini Mu insert is used together with an oligonucleotide universal primer of Mu-end sequence in the base specific chain termination method of Sanger et al, supra. The entire process of in vivo transposition is carried out in less than a day. On the next day, each mini Mu insert phage is grown, the viral DNA is prepared, and the sequence reactions and gel electrophoresis are carried out. Typically, the autoradiograph of the gel can be read on the third or fourth day to obtain the sequence. Thus, the entire sequencing analysis and identification can be accomplished within about 2 to 4 days.

In addition, one can also map the point of mini Mu insertion in each mini Mu insert by a restriction fragment analysis of the replicative form DNA, using restriction sites within the mini Mu DNA. For example, pAT38 has one EcoRl site and one XhoI site in the mini Mu part. This analysis is useful if one wishes to minimize the number of sequencing reactions and gel electrophoresis by pre-screening and choosing a set of mini Mu inserts in the library such that the mini Mu insertion site on each member of the set is separated by several hundred base pairs from that of its neighbors. Otherwise, mapping of the insertion site can be postponed until a reasonable number of mini Mu inserts have been sequenced and a few remaining gaps have to be filled in. In this case, the unused member of the library can be screened to fish out the ones that can fill the gaps.

The library of mini Mu inserts obtained in accordance with the present invention is also useful for other purposes. For example, it can be used for the study of gene inactiviation by insertion mutation, or as an intermediate for trimming and recloning purposes. For instance, if two sets of clones are generated with different orientation of the cloned segment of DNA of interest, then annealing of a pair of mini Mu inserts, one each from each set, followed by mung beam nuclease digestion, will generate a double strand DNA fragment whose ends are almost precisely at the mini insertion sites in the pair of subclones. The DNA fragment thus generated can be cloned into any convenient cloning vector if desired.

The importance and utility of a rapid and accurate method of DNA base sequence determination is of fundamental nature both for biological sciences as well as for genetic engineering processes. Growth, development and differentiation in all organisms including eukaryotic organisms, are directed by genetically controlled factors and the genes are nothing more than an assemblage of a particular sequence and number of purine and pyrimidine bases. The method of the present invention makes it much simpler to decipher the secret encoded in the DNAs in a known chemical language within a matter of few hours, less than 96 hours.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A plasmid having a mini Mu transposon of less than 2 kilobases inserted in plasmid DNA.

2. The plasmid of claim 1 being incorporated in ATCC 39943.

3. A method of determining base sequence in a DNA segment comprising:
   (a) cloning said DNA segment by incorporation thereof in a cloning vector selected from the group consisting of ColE1 plasmids and M13 DNA phages;
   (b) randomly inserting a mini Mu marker transposon of less than 2 kilobases in cloned DNA of step (a);
   (c) isolating transposon-containing DNA obtained through step (b);
   (d) separating radiolabelled chain terminator reaction products obtained by using radiolabelled nucleotides as precursors and the DNA of step (c) as a template together with universal primer oligonucleotide having sequence complimentary to one of the transposon ends or two oligonucleotides each complimentary to each of the two ends of the tramsposon; and
   (e) identifying the sequence of said bases from said radiolabelled products through suitable gel elctrophoretic means.

4. The method of claim 3 wherein said transposon has two end sequences of Mu phage DNA.

5. The method of claim 4 wherein said transposon has a drug resistance marker.

6. The method of claim 5 employing suitable *Escherichia coli* strains as a vehicle for phage multiplication and transposition reactions.

7. The method of claim 6 wherein said electrophoretic means is denaturing acrylamide gel electrophoresis.

8. The method of claim 7 wherein radiolabelled products are identified by autoradiographic means, optionally employing computer means.

9. A method of sequencing a DNA segment comprising:
   (a) cloning said DNA segment in a M13 phage and preparing a stock of said phage having said DNA cloned therein;
   (b) infecting with said phage stock a suitable *Escherichia coli* strain having plasmid carrying mini Mu transposons and ampicillin resistant marker therein;
   (c) selecting ampicillin resistant phage particles having said transposons randomly incorporated in the cloned DNA during step (b);
   (d) extracting substantially purified DNA from said ampicillin resistant phage particles and employing said purified DNA as a template in a suitable chain terminator reaction using radiolabelled DNA precursors to obtain radiolabelled products; and
   (e) identifying base sequence from said radiolabelled products by gel electrophoretic, autoradiographic and computer means.

10. The plasmid of claim 1 wherein said mini mu has drug resistant markers.

11. The method of claim 3 determining the base sequence from inside toward outside of the DNA segment of step (a).

12. The method of claim 3 completing the entire process in less than 96 hours.

* * * * *